(12) United States Patent
Suwa et al.

(10) Patent No.: US 11,312,942 B2
(45) Date of Patent: Apr. 26, 2022

(54) MATERIAL-FIXING SUBSTRATE AND METHOD FOR PRODUCING SAME, AND MATERIAL-FIXING AGENT USED FOR MATERIAL-FIXING SUBSTRATE

(71) Applicant: SONY CORPORATION, Tokyo (JP)

(72) Inventors: Shunichi Suwa, Kanagawa (JP);
Kunihiko Nagamine, Kanagawa (JP);
Masahiro Matsumoto, Kanagawa (JP);
Daisuke Yamaguchi, Kanagawa (JP);
Yoshio Goto, Kanagawa (JP); Kyohei Yoshimitsu, Tokyo (JP)

(73) Assignee: SONY CORPORATION, Tokyo (JP)

( * ) Notice: Subject to any disclaimer, the term of this patent is extended or adjusted under 35 U.S.C. 154(b) by 348 days.

(21) Appl. No.: 16/303,987

(22) PCT Filed: May 2, 2017

(86) PCT No.: PCT/JP2017/017263
§ 371 (c)(1),
(2) Date: Nov. 21, 2018

(87) PCT Pub. No.: WO2017/212838
PCT Pub. Date: Dec. 14, 2017

(65) Prior Publication Data
US 2020/0318076 A1 Oct. 8, 2020

(30) Foreign Application Priority Data
Jun. 8, 2016 (JP) .............................. JP2016-114424

(51) Int. Cl.
| | | |
|---|---|---|
| *C12N 5/09* | (2010.01) |
| *C07D 403/04* | (2006.01) |
| *C07D 225/02* | (2006.01) |
| *G01N 33/543* | (2006.01) |
| *C07K 17/00* | (2006.01) |
| *G01N 33/50* | (2006.01) |

(52) U.S. Cl.
CPC ....... *C12N 5/0694* (2013.01); *G01N 33/5005* (2013.01)

(58) Field of Classification Search
CPC .............. C12N 5/0694; G01N 33/5005; C07D 403/04; C07D 225/02; C07K 17/00
See application file for complete search history.

(56) References Cited

U.S. PATENT DOCUMENTS

2003/0219889 A1* 11/2003 Sumaru ................. C12M 47/04
435/287.1
2010/0297250 A1 11/2010 Boons et al.

FOREIGN PATENT DOCUMENTS

| CN | 101925366 A | 12/2010 |
|---|---|---|
| EP | 2222341 A1 | 9/2010 |
| JP | 2011-504507 A | 2/2011 |
| WO | 2009/067663 A1 | 5/2009 |

OTHER PUBLICATIONS

Agard, et al., "A Strain-Promoted [3+2] Azide-Alkyne Cycloaddition for Covalent Modification of Biomolecules in Living Systems", 2004 American Chemical Society, Aug. 19, 2004, 15046-15047 pages.
Baskin, et al., "Copper-Free Click Chemistry for Dynamic in Vivo Imaging", PNAS, vol. 104, No. 43, Sep. 7, 2007, 16793-16797 pages.
Codelli, et al., "Second-Generation Difluorinated Cyclooctynes for Copper-Free Click Chemistry", 2008 American Chemical Society, May 1, 2008, 11486-11493 pages.
Debets, et al., "Aza-Dibenzocyclooctynes for Fast and Efficient enzyme PEGylation Via Copper-Free (3+2) Cycloaddition", The Royal Society of Chemistry 2010, Oct. 22, 2009, 97-99 pages.
Jewett, et al., "Rapid Cu-Free Click Chemistry with Readily Synthesized Biarylazacyclooctynones", 2010 American Chemical Society, Jan. 8, 2010, 3688-3690 pages.
Vaselli, et al., ""On-Off" RGD Signaling Using Azobenzene Photoswitch-Modified Surfaces", ChemPlusChem 2015, 1547-1555 pages.
Kim, et al., "Photoresponsive Carbohydrate-based Giant Surfactants: Automatic Vertical Alignment of Nematic liquid Crystal for the Remote Controllable Optical Device", 2015 American Chemical Society , 6195-6204 pages.
Saito, et al., "Critical Evaluation and Rate Constants of Chemoselective Ligation Reactions for Stoichiometric Conjugations in Water", 2015 American Chemical Society, 1026-1033 pages.
Ning, et al., "Visualizing Metabolically Labeled Glycoconjugates of Living Cells by Copper-Free and Fast Huisgen Cycloadditions", Angew. Chem. Int. Ed. 2008, 2253-2255 pages.
Vaselli, et al., "On-Off RGD Signaling Using Azobenzene Photoswitch-Modified Surfaces" ChemPlusChem 2015, Apr. 23, 2015, 1547-1555 pages.
Baskin, et al., "Copper-Free Click Chemistry for Dynamic in Vivo Imaging", PNAS vol. 104, No. 43, Oct. 23, 2007, 16793-16797 pages.

(Continued)

*Primary Examiner* — Tracy Vivlemore
*Assistant Examiner* — Nam P Nguyen
(74) *Attorney, Agent, or Firm* — Chip Law Group

(57) ABSTRACT

Provided is a material-fixing substrate that does not have to use copper as a catalyst because the substrate-bonding site includes a cyclic alkyne to form a covalent bond with a surface of the substrate, and therefore that can reduce damage to a cell, for example, in a case where a to-be-fixed material is the cell. The material-fixing substrate has a to-be-fixed material fixed thereon via a material-fixing agent. The material-fixing agent includes: a substrate-bonding site that forms a covalent bond with a surface of the substrate and includes at least a cyclic alkyne; a hydrophilic site that is bonded to the substrate-bonding site; a light-responsive site that is bonded to the hydrophilic site and changes the skeleton thereof by irradiation with light; and an attachment site to which the to-be-fixed material is attached.

7 Claims, 4 Drawing Sheets

(56) References Cited

OTHER PUBLICATIONS

Debets, et al., "Aza-dibenzocyclooctynes for fast and efficient enzyme PEGylation via copper-free (3+2) cycloaddition", Chem. Commun, 2010, Nov. 6, 2009, 97-99 pages.

Jewett, et al., "Rapid Cu-Free Click Chemistry with Readily Synthesized Biarylazacyclooctynones", 2010 American Chemical Society, vol. 132, No. 11, Jan. 8, 2010 3688-3690 pages.

Codelli, et al., "Second-Generation Difluorinated Cyclooctynes for Copper-Free Click Chemistry", 2008 American Chemical Society, vol. 130, No. 34, May 1, 2008, 11486-11493 pages.

Saito, et al., "Critical Evaluation and Rate Constants of Chemoselective Ligation Reactions for Stoichiometric Conjugations in Water", 2015 Amercian Chemical Society, Jan. 9, 2015, 1026-1033 pages.

Kim, et al., "Photoresponsive Carbohydrate-based Giant Surfactants: Automatic Vertical Alignment of , Nematic liquid Crystal for the Remote-Controllable Optical Device", :2015 Amercian Chemical Society, Mar. 4, 20156195-6204 pages.

Ning, et al., "Visualizing Metabolically Labeled Glycoconjugates of Living Cells by Coppe-Free and Fast Huisgen Cycloadditions", Angew. Chem. Int. Ed. :2008, Feb. 14, 2008, 2253-2255 pages.

Agard, et al., "A Strain-Promoted [3+2] Azide-Alkyne Cycloaddition for Covalent Modification of Biomolecules in Living Systems", 2004 American Chemical Society, vol. 126, N. 46, Aug. 19, 2004, 15046-15047 pages.

Ning, et al., "Visualizing Metabolically Labeled Glycoconjugates of Living Cells by Copper-Free and Fast Huisgen Cycloadditions", Angew. Chem. Int. Ed. 2008, vol. 47, No. 12, 2253-2255 pages.

Kim, et al., "Photoresponsive Carbohydrate-based Giant Surfactants: Automatic Vertical Alignment of Nematic liquid Crystal for the Remote Controllable Optical Device", ACS Applied materials & interfaces, 2015, vol. 12,No. 6, pp. 2114-2125.

Saito, et al., "Critical Evaluation and Rate Constants of Chemoselective Ligation Reactions for Stoichiometric Conjugations in Water", ACS Chemical Biology, 2015, vol. 10, No. 4, 1026-1033 pages.

Montanez, et al., "Bifunctional Dendronized Cellulose Surfaces as Biosensors", Biomacromolecules, 2011, vol. 12, No. 6, 2114-2125 pages.

International Search Report and Written Opinion of PCT Application No. PCT/JP2017/017263, dated Aug. 1, 2017, 9 pages of ISRWO.

Mushokubai Click Hanno Soshi Kokinosei Alkin [online], Apr. 2016, pp. 1 to 4, [retrieval date Jul. 7, 2017 (Jul. 7, 2017)], Internet: <URL:http://www.kanto.co.jp/products/siyaku/images/s click reagent OAI-01.pdf>, particularly pp. 2 to 3.

Atsushi Shimoyama, "Kininatta Ronbun", Seimei Kagaku Kenkyu Letter, 2010, No. 34, pp. 16 to 20, pp. 16 to 17.

Sono Ni Azide to Alkyne tono Click Hanno: Yuki K agaku Hanno ga Motarashita Seimei Kagaku Kenkyu nl Okeru Kakushin [online], May 31, 2016 (May 31, 2016), [retrieval date Jul. 7, 2017 (Jul. 7, 2017)], Internet: <URL:http://chembiolab.sakura.ne.jp/Topics-2-2.html>, <https://web.archive.org/web/20160531045218/http:/1chembiolab.sakura.ne.jp/Topics-2-2.html>, a whole article.

* cited by examiner

MATERIAL-FIXING SUBSTRATE AND METHOD FOR PRODUCING SAME, AND MATERIAL-FIXING AGENT USED FOR MATERIAL-FIXING SUBSTRATE

CROSS REFERENCE TO RELATED APPLICATIONS

This application is a U.S. National Phase of International Patent Application No. PCT/JP2017/017263 filed on May 2, 2017, which claims priority benefit of Japanese Patent Application No. JP 2016-114424 filed in the Japan Patent Office on Jun. 8, 2016. Each of the above-referenced applications is hereby incorporated herein by reference in its entirety.

TECHNICAL FIELD

The present technology relates to a material-fixing substrate and a method for producing the same, and a material-fixing agent used for the material-fixing substrate. More specifically, the present technology relates to a material-fixing substrate and the like capable of reducing physical property damage to a to-be-fixed material.

BACKGROUND ART

Technology of a material-fixing substrate is used, for example, for selection of a rare cell, quality control of a multifunctional stem cell (such as an iPS cell or an ES cell), and the like.

As this technology using a material-fixing substrate, for example, technology is known in which a photodegradable linker or a photoisomerization material as a material-fixing agent is fixed on a surface of the substrate, and a to-be-fixed material can be attached and detached by light stimulation.

As this type of technology using a material-fixing substrate, technology disclosed in Non-Patent Document 1 is known. In this technology disclosed in Non-Patent Document 1, a photoisomerization material having an azobenzene skeleton as a material-fixing agent is fixed on a substrate. Specifically, the photoisomerization material is fixed on the substrate by a click reaction between an alkyne constituting the photoisomerization material and an azide group modified to a surface of the substrate.

In addition, Patent Document 1 discloses that Cu(I) that catalyzes 1,3-dipolar cycloaddition of a terminal alkyne-containing azide to provide a stable triazole is used for tagging various biomolecules including a protein, a nucleic acid, a lipid, and a monosaccharide. Technology similar to this technology is also disclosed in Non-Patent Documents 2 to 6.

CITATION LIST

Patent Document

Patent Document 1: Japanese Translation of PCT International Application Publication No. 2011-504507

Non-Patent Document

Non-Patent Document 1: E. Vaselli, ChemPlusChem, 80, 1547-1555, 2015
Non-Patent Document 2: N. J. Agard, C. R. Bertozzi et al., J. Am. Chem. Soc., 126, 15046-15047, 2004
Non-Patent Document 3: J. M. Baskin, C. R. Bertozzi et al., PNAS, 104, 43, 16793-116797, 2007
Non-Patent Document 4: J. A. Codelli, C. R. Bertozzi, J. Am. Chem. Soc., 130, 11486-11493, 2008
Non-Patent Document 5: M. F. Debets, F. L. van Delft et al., Chem. Commun., 46, 97-99, 2010
Non-Patent Document 6: J. C. Jewett, C. R. Bertozzi et al., J. Am. Chem. Soc., 132, 3688-3690, 2010

SUMMARY OF THE INVENTION

Problems to be Solved by the Invention

However, in conventional technology using a material-fixing substrate, particularly in the technology disclosed in Non-Patent Document 1, in a case where a to-be-fixed material is a cell, copper that is toxic to the cell is used as a catalyst. Therefore, even if the cell can be detached, the detached cell is damaged disadvantageously. Furthermore, the detached cell cannot be secondarily used, for example, for culture after the cell is detached and recovered.

Solutions to Problems

The present technology provides a material-fixing substrate having a to-be-fixed material fixed thereon via a material-fixing agent, in which the material-fixing agent includes: a substrate-bonding site that forms a covalent bond with a surface of the substrate and includes at least a cyclic alkyne; a hydrophilic site that is bonded to the substrate-bonding site; a light-responsive site that is bonded to the hydrophilic site and changes the skeleton thereof by irradiation with light; and an attachment site to which the to-be-fixed material is attached.

In the material-fixing substrate according to the present technology, the cyclic alkyne may have a structure selected from the group consisting of a benzocyclooctynyl group, a difluorocyclooctynyl group, a dibenzocyclooctynyl group, an azadibenzocyclooctynyl group, a biarylazacyclooctynonyl group, and derivatives thereof.

In addition, in the material-fixing substrate according to the present technology, the light-responsive site may have one or more structures selected from the group consisting of azobenzene, stilbene, spiropyran, spirooxazine, fulgide, cinnamate, cinnamoyl, oryzanol, and diarylethene.

Furthermore, in the material-fixing substrate according to the present technology, the hydrophilic site may include polyethylene oxide or polyalkylene oxide.

In addition, in the material-fixing substrate according to the present technology, the material-fixing agent may have any one structural formula selected from the following chemical formulas 1 to 7. Here, in the formulas, $R^1$ to $R^8$ are each independently selected from the group consisting of a hydrogen atom, a halogen atom, a hydroxy group, an alkoxy group, and an alkyl group having 1 to 10 carbon atoms, $R^9$ is the to-be-fixed material, $X^1$ is selected from the group consisting of $CH_2$, $C=O$, $C=N-OR^{10}$, $C=N-NR^{10}R^{11}$, $CHOR^{10}$, and $CHNHR^{10}$, $X^2$ and $X^3$ are each a hydrogen atom or a halogen atom, $R^{10}$ and $R^{11}$ are each a hydrogen atom or an alkyl group having 1 to 10 carbon atoms, j is an integer of 1 to 5, k is an integer of 2 to 100, l is an integer of 1 or 2, m is an integer of 1 to 3, and n is an integer of 2 to 100.

[Chemical Formula 1]
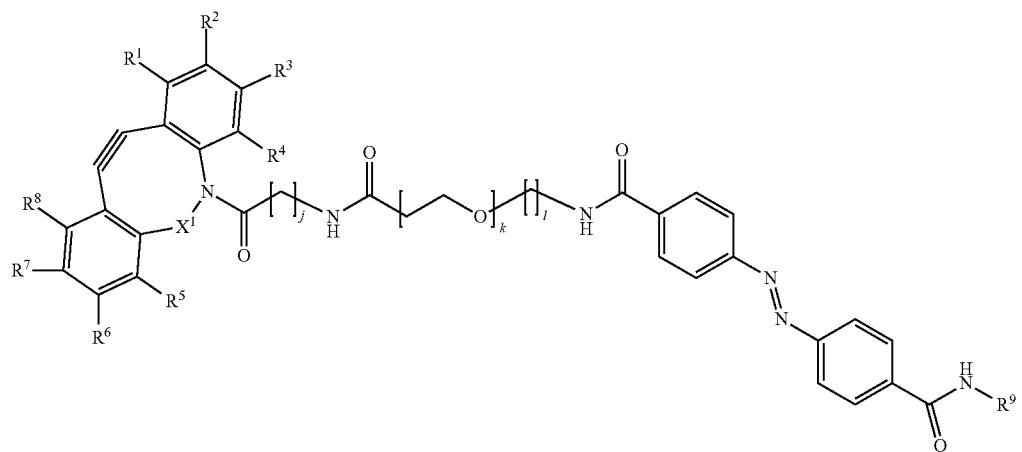
[Chemical Formula 2]
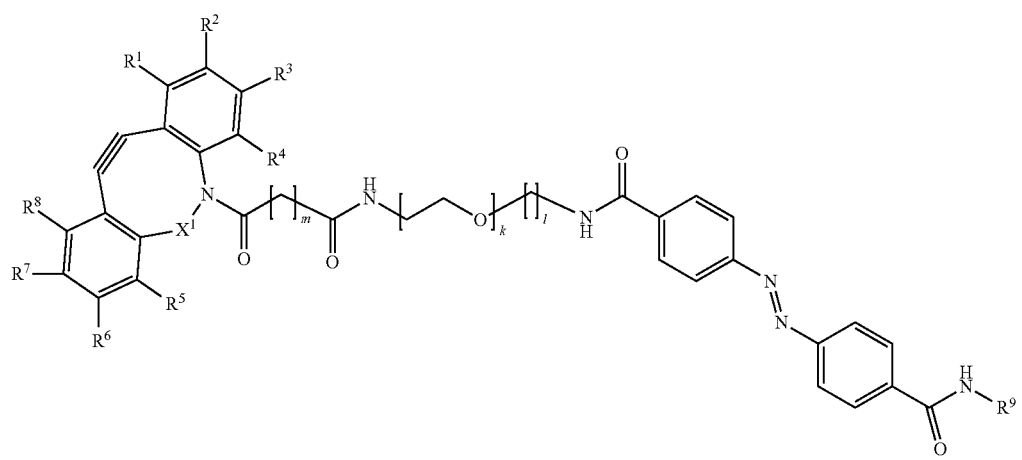
[Chemical Formula 3]
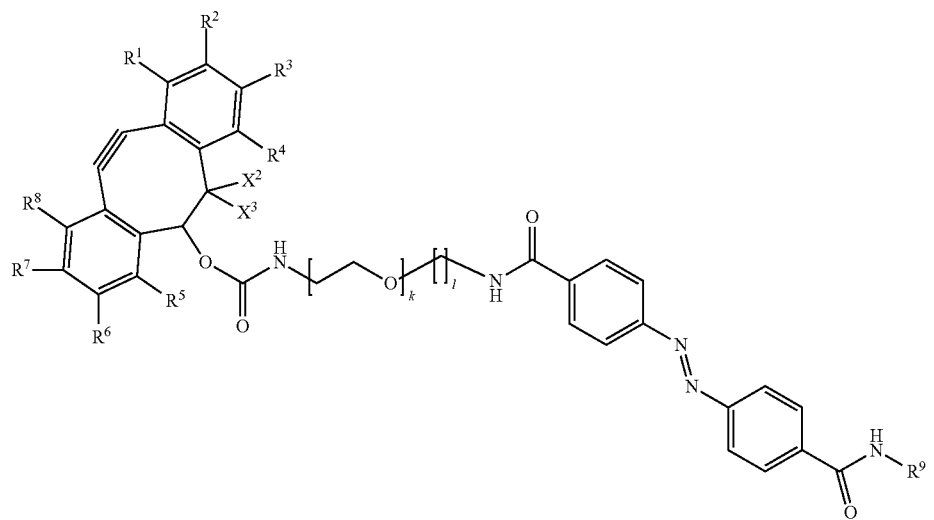

-continued
[Chemical Formula 4]
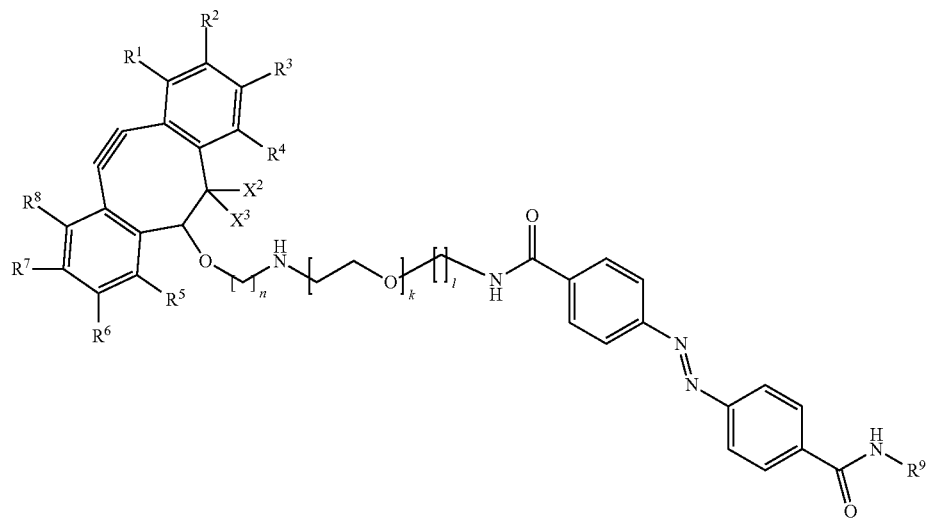
[Chemical Formula 5]
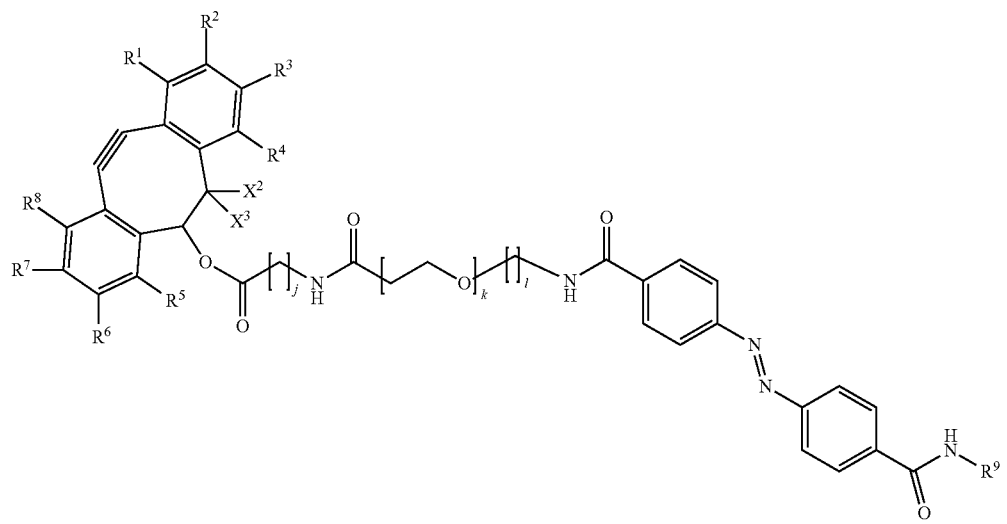
[Chemical Formula 6]
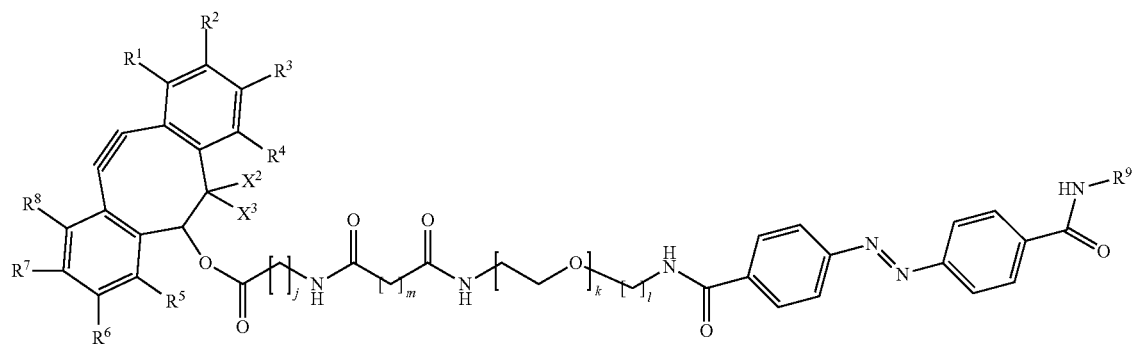

-continued

[Chemical Formula 7]

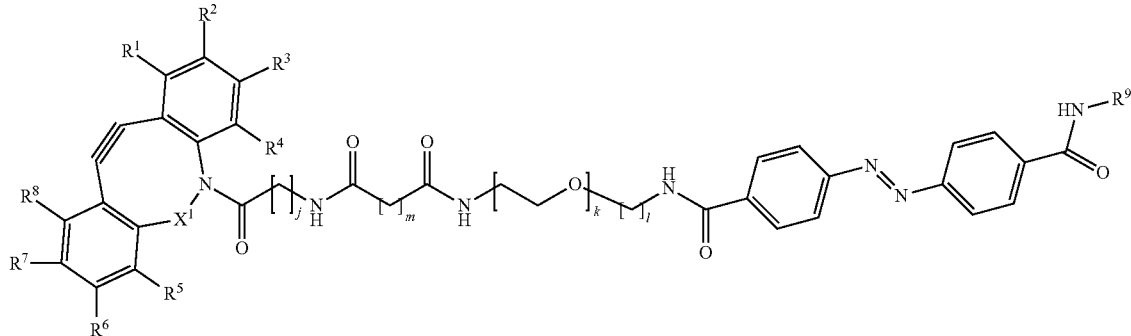

In addition, in the material-fixing substrate according to the present technology, the to-be-fixed material may be at least one selected from the group consisting of an antibody, collagen, laminin, fibronectin, a protein or a peptide containing a part of the protein, and a saccharide.

Furthermore, in the material-fixing substrate according to the present technology, an azide group to be bonded to the substrate-bonding site may be modified to a surface of the substrate.

In addition, the present technology also provides a material-fixing agent for fixing a to-be-fixed material on a substrate, including: a substrate-bonding site that forms a covalent bond with a surface of the substrate and includes at least a cyclic alkyne; a hydrophilic site that is bonded to the substrate-bonding site; a light-responsive site that is bonded to the hydrophilic site and changes the skeleton thereof by irradiation with light; and an attachment site to which the to-be-fixed material is attached.

Furthermore, the present technology also provides a method for producing a material-fixing substrate, including: a modification step of modifying an azide group to a surface of a substrate; and an application step of applying, to the substrate, a material-fixing agent including: a substrate-bonding site that forms a covalent bond with a surface of the substrate and includes at least a cyclic alkyne; a hydrophilic site that is bonded to the substrate-bonding site; a light-responsive site that is bonded to the hydrophilic site and changes the skeleton thereof by irradiation with light; and an attachment site to which a to-be-fixed material is attached.

Effects of the Invention

According to the present technology, copper does not have to be used as a catalyst because the substrate-bonding site includes a cyclic alkyne to form a covalent bond with a surface of a substrate. Therefore, for example, in a case where a to-be-fixed material is a cell, damage to the cell can be reduced.

Note that the effects described herein are not necessarily limited, and may be any of the effects described in the present technology.

MODE FOR CARRYING OUT THE INVENTION

Hereinafter, preferred embodiments for carrying out the present technology will be described with reference to the drawings. The embodiments described below exemplify representative embodiments of the present technology, and the scope of the present technology is not narrowly interpreted by the embodiments. Note that the description will be made in the following order.

1. Material-fixing substrate according to the present technology
(1) Substrate
(2) Material-fixing agent layer
(2-1) Substrate-bonding site
(2-2) Hydrophilic site
(2-3) Light-responsive site
(2-4) Attachment site
(3) To-be-fixed material
2. Method for producing material-fixing substrate according to the present technology
(1) Modification step
(2) Application step
3. Method for selecting to-be-fixed material according to the present technology
(1) To-be-fixed material attachment step
(2) Chemical introduction step
(3) First light irradiation step
(4) Second light irradiation step
(5) Liquid-feeding step
(6) Recovery step
(7) Third light irradiation step <1. Material-Fixing Substrate According to the Present Technology>

Figure 1:
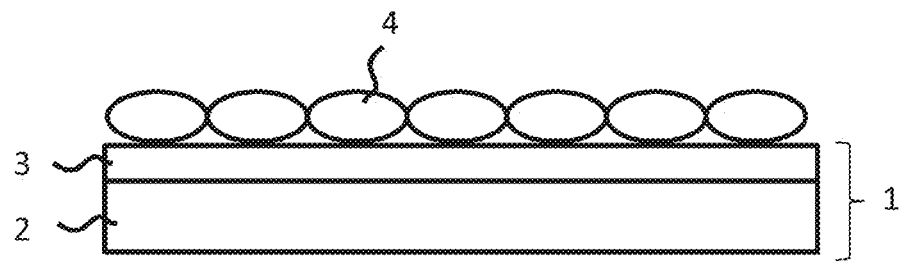
FIG. 1 is a schematic diagram schematically illustrating a first embodiment of a material-fixing substrate according to the present technology.
Figure 2:
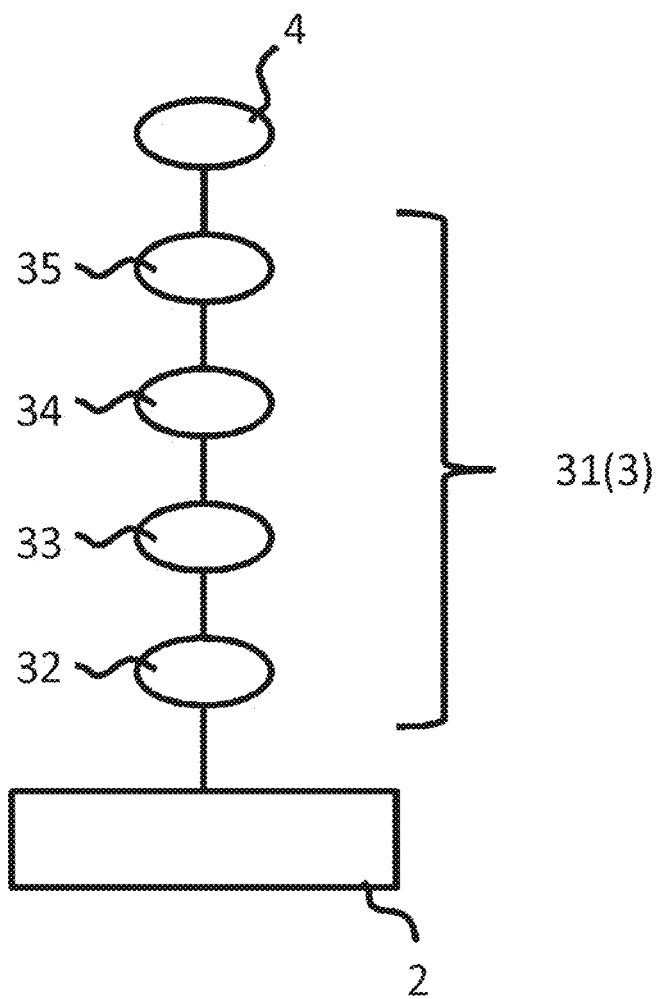
FIG. 2 is a schematic diagram schematically illustrating a material-fixing agent included in the material-fixing substrate illustrated in FIG. 1.

With reference to FIGS. 1 and 2, a material-fixing substrate according to the present technology will be described. A material-fixing substrate 1 according to the present technology includes a substrate 2 and a material-fixing agent layer 3. To a surface of this material-fixing substrate 1, a to-be-fixed material 4 is attached, and the material-fixing substrate 1 is used for recovering the to-be-fixed material 4.

Note that the material-fixing substrate 1 illustrated in FIG. 1 has a flat plate shape, but may have any shape as long as the material-fixing agent layer 3 is disposed on a surface of the substrate 1, and may have another shape, for example, a particle shape or the like.

Hereinafter, the substrate 2 and the material-fixing agent layer 3 will be described.

(1) Substrate

The substrate 2 is preferably constituted by a material having a flat surface and transmitting light, such as a glass plate, a quartz plate, or various plastic plates, for example. By using a light-transmitting material, it is possible to observe the to-be-fixed material 4 irradiated with light or attached via the substrate 2.

In addition, in this substrate 2, a surface in contact with the material-fixing agent layer 3 is attached to a material-fixing agent constituting the material-fixing agent layer 3.

Specifically, an azide group or an aromatic azide group is modified to a surface of the substrate 2 by a bonding member such as a silane coupling agent, and the azide group or the aromatic azide group forms a covalent bond with a terminal of the material-fixing agent. The to-be-fixed material 4 is attached to the material-fixing agent attached in this way.

Therefore, the substrate 2 according to the present technology may have an introduction hole for introducing the to-be-fixed material 4 into the substrate 2 and a recovery hole for recovering the to-be-fixed material 4.

(2) Material-Fixing Agent Layer

Meanwhile, the material-fixing agent layer 3 is constituted by a material-fixing agent fixed to the substrate 2. As illustrated in FIG. 2, this material-fixing agent 31 roughly includes a substrate-bonding site 32, a hydrophilic site 33, a light-responsive site 34, and an attachment site 35. Each of the sites will be described below.

(2-1) Substrate-Bonding Site

The substrate-bonding site 32 is a site for bonding the substrate 2 to the material-fixing agent 31. This substrate-bonding site 32 preferably includes a group having a low attachment property to the to-be-fixed material 4 so as not to inhibit attachment of the to-be-fixed material 4 to a to-be-fixed material-attaching terminal included in the attachment site 35. Meanwhile, as a bonding portion to the substrate 2, the substrate-bonding site 32 preferably includes a cyclic alkyne easily bonded to an azide group or an aromatic azide group modified to a surface of the substrate 2 through a click reaction.

Furthermore, the cyclic alkyne more preferably has a structure selected from the group consisting of a benzocyclooctynyl group, a difluorocyclooctynyl group, a dibenzocyclooctynyl group, an azadibenzocyclooctynyl group, a biaryl azacyclooctynonyl group, and derivatives thereof.

Examples of such a substrate-bonding site 32 including at least a cyclic alkyne include those represented by the following chemical formulas 8 to 18. Note that the structural formulas illustrated in the following chemical formulas 8 to 18 are merely examples.

[Chemical Formula 8]

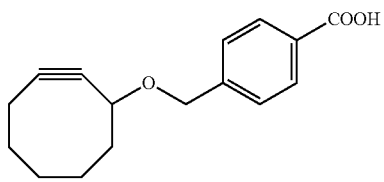

[Chemical Formula 9]

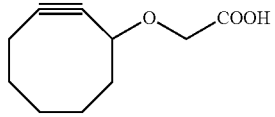

[Chemical Formula 10]

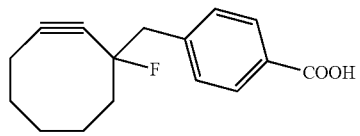

[Chemical Formula 11]

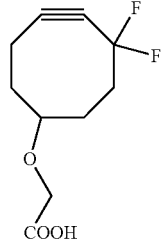

[Chemical Formula 12]

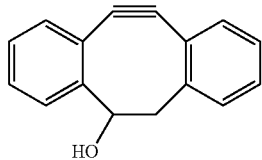

[Chemical Formula 13]

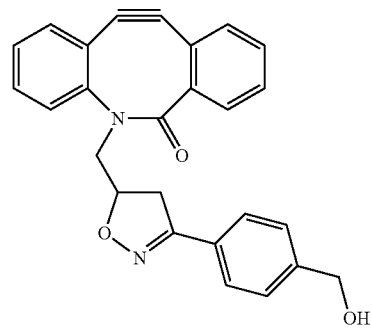

[Chemical Formula 14]

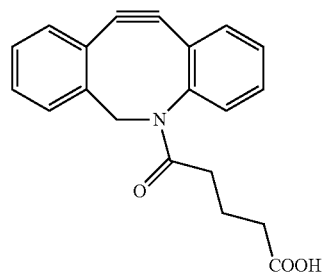

[Chemical Formula 15]

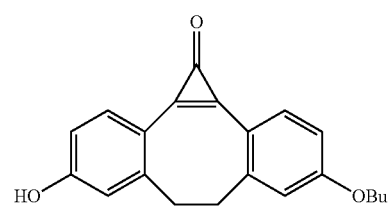

[Chemical Formula 16]

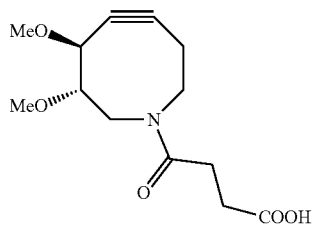

[Chemical Formula 17]

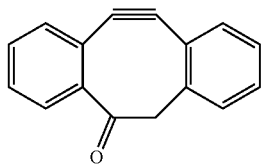

[Chemical Formula 18]

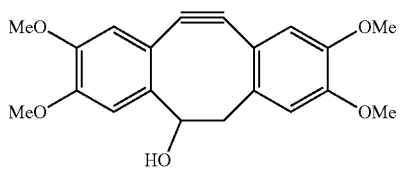

(2-2) Hydrophilic Site

Next, the hydrophilic site 33 included in the material-fixing agent 31 will be described.

The hydrophilic site 33 is bonded to the substrate-bonding site 32. This hydrophilic site 33 is not particularly limited, but for example, preferably includes polyethylene oxide or another polyalkylene oxide.

(2-3) Light-Responsive Site

The material-fixing agent according to the present technology includes the light-responsive site 34 that is isomerized by irradiation with light.

This light-responsive site 34 is bonded to the hydrophilic site 33 and includes a group (hereinafter referred to as "light-responsive group") that changes the structure thereof by irradiation with light.

That is, by irradiation with light, the light-responsive site 34 changes the structure thereof (is isomerized), and the to-be-fixed material 4 can be thereby recovered from the substrate 2.

The light-responsive group is not particularly limited, but examples thereof include azobenzene, stilbene, spiropyran, spirooxazine, fulgide, cinnamate, cinnamoyl, oryzanol, diarylethene, derivatives thereof, and the like. Among these groups, one or a combination of two or more can be used. Among these groups, it is preferable to include azobenzene having a relatively large reaction rate of photoisomerization.

In addition, in a case where the light-responsive site 34 has two or more light-responsive groups, the light-responsive groups can be arranged in series. In such a case, photoisomerization occurs in at least two or more places by irradiation with light. As a result, the to-be-fixed material 4 is easily detached from the substrate 2.

(2-4) Attachment Site

The material-fixing agent according to the present technology includes the attachment site 35 that is bonded to the light-responsive site 34. One end of this attachment site 35 is bonded to the light-responsive site 34, and a terminal of the attachment site 35 is formed as a to-be-fixed material-attaching terminal to be bonded to the to-be-fixed material 4. In order to selectively attach the to-be-fixed material 4 to the to-be-fixed material-attaching terminal, the to-be-fixed material-attaching terminal is preferably constituted by a group having a high attachment property to the to-be-fixed material 4, and the other portion is preferably constituted by a group having a low attachment property to the to-be-fixed material 4.

The group for forming the to-be-fixed material-attaching terminal is not particularly limited, and examples thereof include an ionic functional group such as an amino group or a carboxyl group, an alkenyl group such as an oleyl group, a GRGDS sequence (Gly-Arg-Asp-Ser) peptide, a protein, and the like.

As the material-fixing agent 31 including the substrate-bonding site 32, the hydrophilic site 33, the light-responsive site 34, and the attachment site 35 as described above, those represented by the following chemical formulas 19 to 25 are considered.

Here, in the formulas, $R^1$ to $R^9$ are each independently selected from the group consisting of a hydrogen atom, a halogen atom, a hydroxy group, an alkoxy group, and an alkyl group having 1 to 10 carbon atoms, $R^9$ is the to-be-fixed material, $X^1$ is selected from the group consisting of $CH_2$, $C=O$, $C=N-OR^{10}$, $C=N-NR^{10}R^{11}$, $CHOR^{10}$, and $CHNHR^{10}$, $X^2$ and $X^3$ are each a hydrogen atom or a halogen atom, $R^{10}$ and $R^{11}$ are each a hydrogen atom or an alkyl group having 1 to 10 carbon atoms, j is an integer of 1 to 5, k is an integer of 2 to 100, l is an integer of 1 or 2, m is an integer of 1 to 3, and n is an integer of 2 to 100.

[Chemical Formula 19]

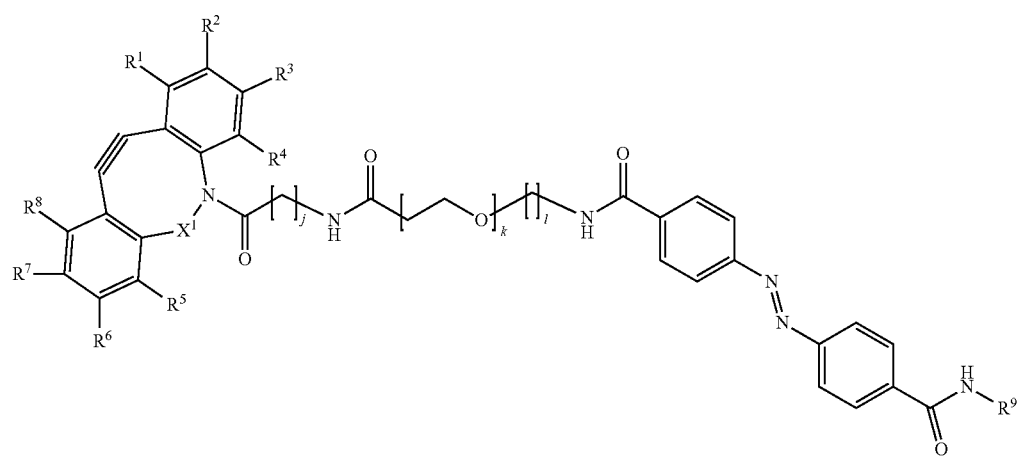

[Chemical Formula 20]
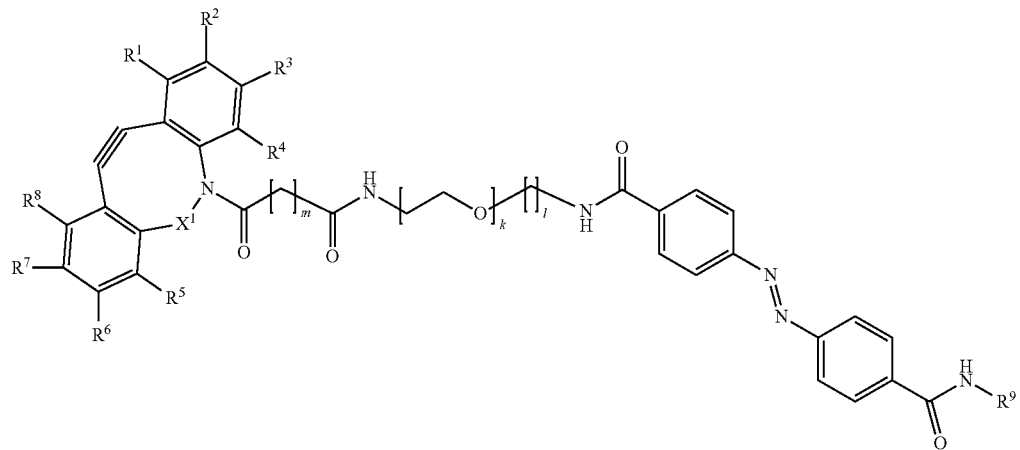
[Chemical Formula 21]
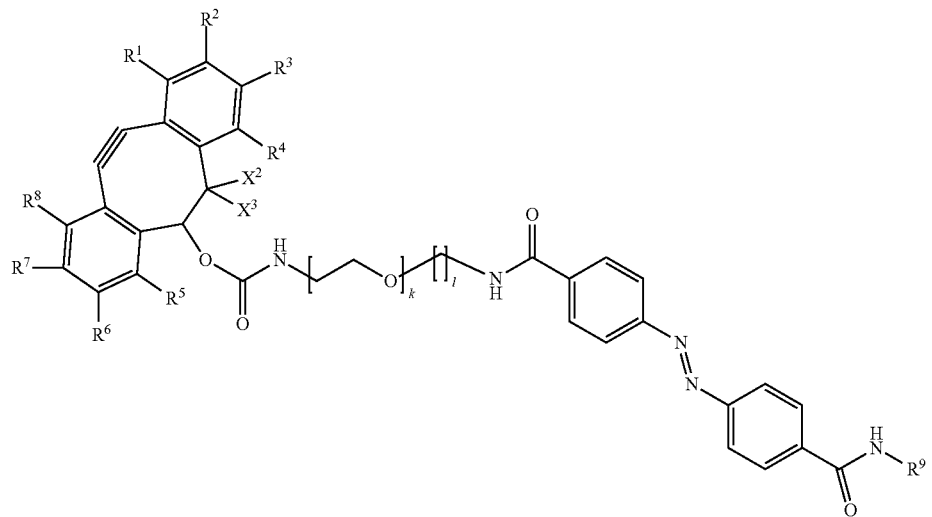
[Chemical Formula 22]
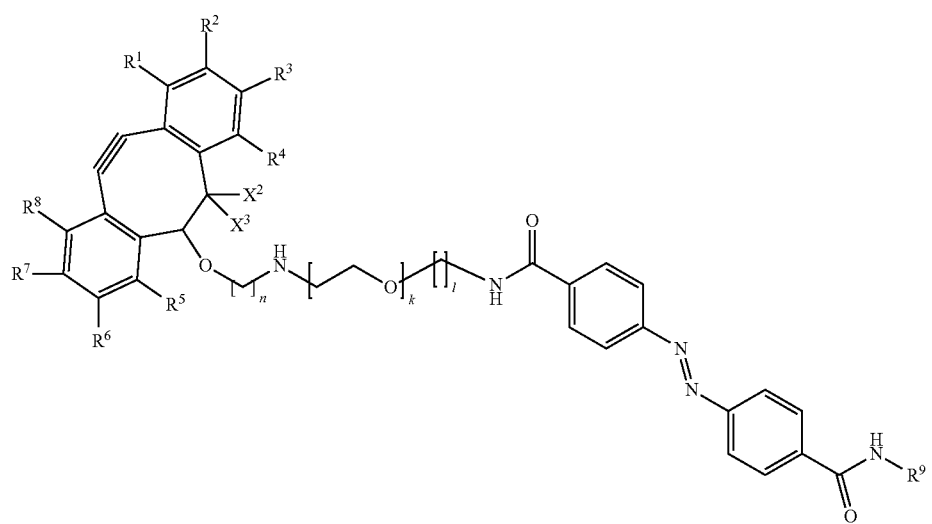

[Chemical Formula 23]
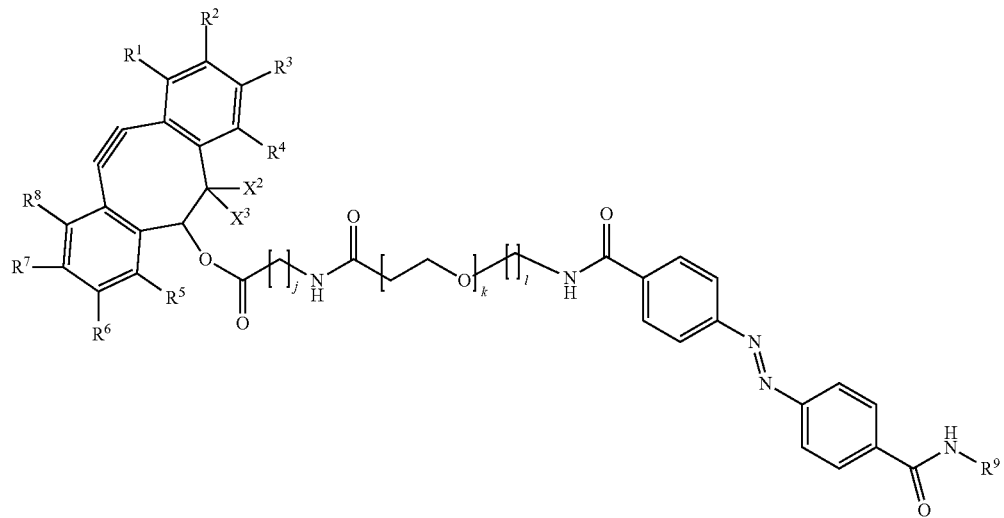
[Chemical Formula 24]
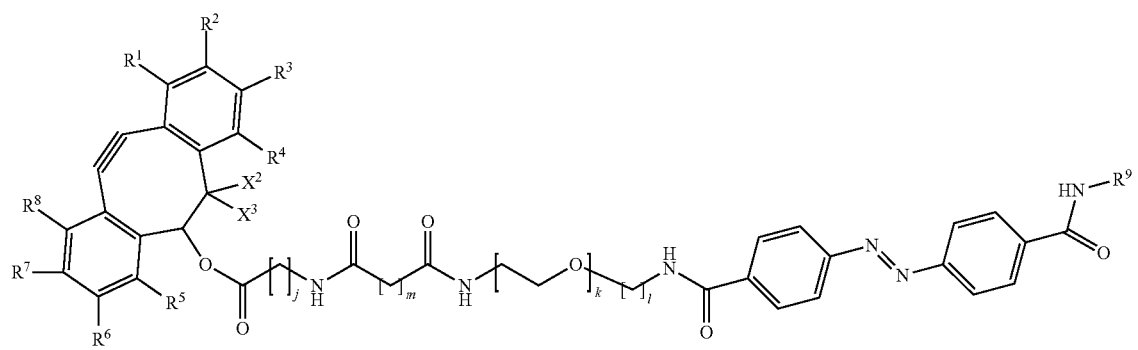
[Chemical Formula 25]
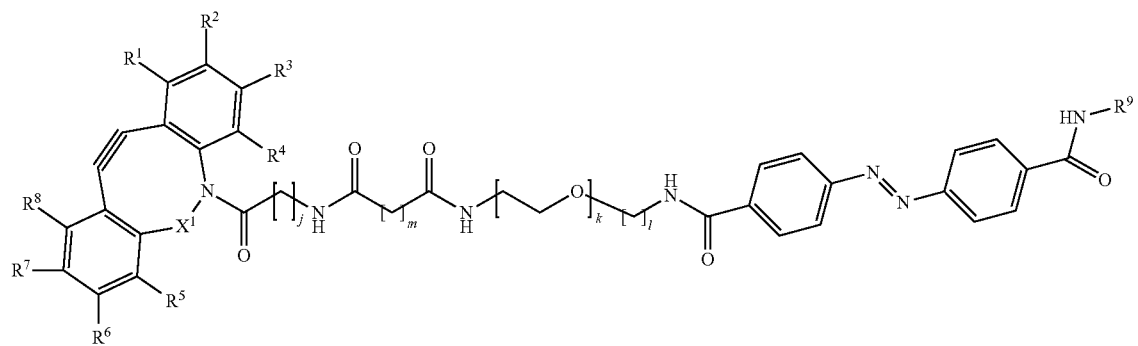

In particular, as the material-fixing agent 31, one represented by the following chemical formula 26 is preferable.

[Chemical Formula 26]

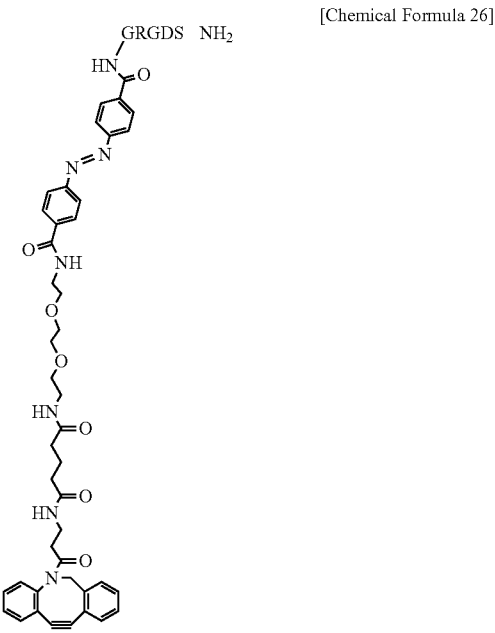

(3) To-be-Fixed Material

The to-be-fixed material 4 is attached to the material-fixing substrate 1 according to the present technology.

The to-be-fixed material 4 is not particularly limited, and examples thereof include a cell, an antibody, collagen, laminin, fibronectin, a protein or a peptide containing a part of the protein, a saccharide, and the like. By applying the material-fixing substrate of the present technology to the cell, the antibody, the collagen, the laminin, the fibronectin, the protein or the peptide containing a part of the protein, and the saccharide, work of recovering and selecting the to-be-fixed material 4 can be performed efficiently.

In the above material-fixing substrate 1 according to the present technology, the substrate-bonding site 32 includes at least a cyclic alkyne. Therefore, the substrate 2 can be bonded to the material-fixing agent layer 3 without using copper as a catalyst. Therefore, for example, in a case where the to-be-fixed material 4 is a cell, damage to the cell can be reduced, and proliferation ability of the cell can be thereby maintained. In addition, copper is not required as a catalyst. Therefore, proliferation ability of a recovered cell can also be maintained.

Furthermore, when the azobenzene is irradiated with ultraviolet light, the azobenzene changes the structure thereof from a trans-form to a cis-form. Meanwhile, when the azobenzene is irradiated with visible light, the azobenzene causes such a reversible change returning from the cis-form to the trans-form. Therefore, in a case where the light-responsive group included in the light-responsive site 34 is azobenzene, the material-fixing substrate 1 according to the present technology can repeatedly detach and recover the to-be-fixed material 4 by being alternately and repeatedly irradiated with light in an ultraviolet region and light in a visible region, and use cost of the material-fixing substrate 1 can be thereby reduced.

<2. Method for Producing Material-Fixing Substrate According to the Present Technology>

Figure 3:
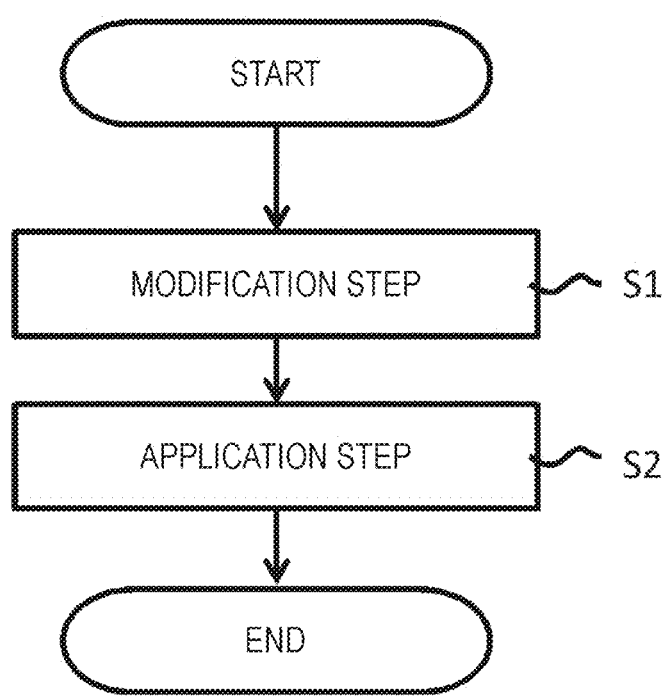
FIG. 3 is a flowchart illustrating a method for producing the material-fixing substrate according to the present technology.

Next, with reference to FIG. 3, a method for producing the material-fixing substrate according to the present technology will be described.

This production method includes at least a modification step S1 and an application step S2. Each of the steps will be described below.

(1) Modification Step

In this modification step S1, an azide group or an aromatic azide group (hereinafter referred to as "azide group or the like") is modified to a surface of the substrate 2 to which the material-fixing agent 31 is attached.

A method for modifying an azide group or the like is not limited, and a known method can be used. Examples of the method include a method using a silane coupling agent. Hereinafter, an example of a modification method will be described according to an operation procedure. Incidentally, in the following description, a modification step in a case where the substrate 2 is a glass plate will be described.

That is, the substrate 2 which is a glass plate is introduced into acetone, and a surface thereof is cleaned by ultrasonic treatment. Thereafter, the substrate 2 is taken out from acetone and dried.

Thereafter, the substrate 2 is subjected to oxygen plasma treatment, and then caused to react with 4 v/v % (3-bromopropyl) trimethoxysilane/toluene which is a silane coupling agent overnight.

Thereafter, the substrate 2 is cleaned with toluene, ethanol and acetone, and then dried in vacuum. Then, the substrate 2 is shaken overnight in 50 mM sodium azide/dimethylformamide.

Thereafter, the substrate 2 is cleaned with dimethylformamide, ethanol, and acetone, and then dried in vacuum. Through these steps, an azide group is modified to a surface of the substrate 2.

(2) Application Step

In the production method according to the present technology, after a surface of the substrate 2 is azidized in the modification step S1, the application step S2 in which the material-fixing agent 31 is applied to the substrate 2 is performed.

In this application step S2, a method for applying the material-fixing agent 31 is not particularly limited, and a known method can be used.

Here, in a case where the substrate-bonding site 32 of the material-fixing agent 31 includes a cyclic alkyne, an azide group or an aromatic azide group modified to a surface of the substrate 2 and the cyclic alkyne form a covalent bond. As a result, the material-fixing agent 31 is attached to the surface of the substrate 2.

<3. Method for Selecting to-be-Fixed Material According to the Present Technology>

Next, a cell selection method using the material-fixing substrate 1 according to the present technology will be described.

This cell selection method includes a to-be-fixed material attachment step S11, a chemical introduction step S12, a first light irradiation step S13, a second light irradiation step S14, a liquid-feeding step S15, and a recovery step S16, and may include a third light irradiation step S17 as necessary. Each of the steps will be described below.

Incidentally, in the following description, a case where the to-be-fixed material 4 is a cell will be described. However, the selection method according to the present technology can be applied even to a case where the to-be-fixed material 4 is not a cell.

(1) To-be-Fixed Material Attachment Step

In the method for selecting a to-be-fixed material according to the present technology, first, the to-be-fixed material attachment step S11 is performed.

In this to-be-fixed material attachment step S11, a cell 4 is injected into the substrate 2, and the cell 4 is attached to the substrate 2. For example, treatment such as centrifugation or incubation is performed to attach the cell 4 to the substrate 2.

(2) Chemical Introduction Step

After the to-be-fixed material attachment step S11 is performed, the chemical introduction step S12 for introducing a specific chemical to the substrate 2 is performed.

In this chemical introduction step S12, a chemical harmful to the non-recovery target cell 4 is introduced into the substrate 2. The type of this chemical is not particularly limited, and one known substance or a combination of two or more known substances may be used depending on the type of the cell 4. For example, in a case where the to-be-fixed material 4 is a human chronic myeloid leukemia cell line K562 cell, Imatinib (trade name: Gleevec) which is a Bcr-Abl tyrosine kinase inhibitor can be used.

Figure 5:
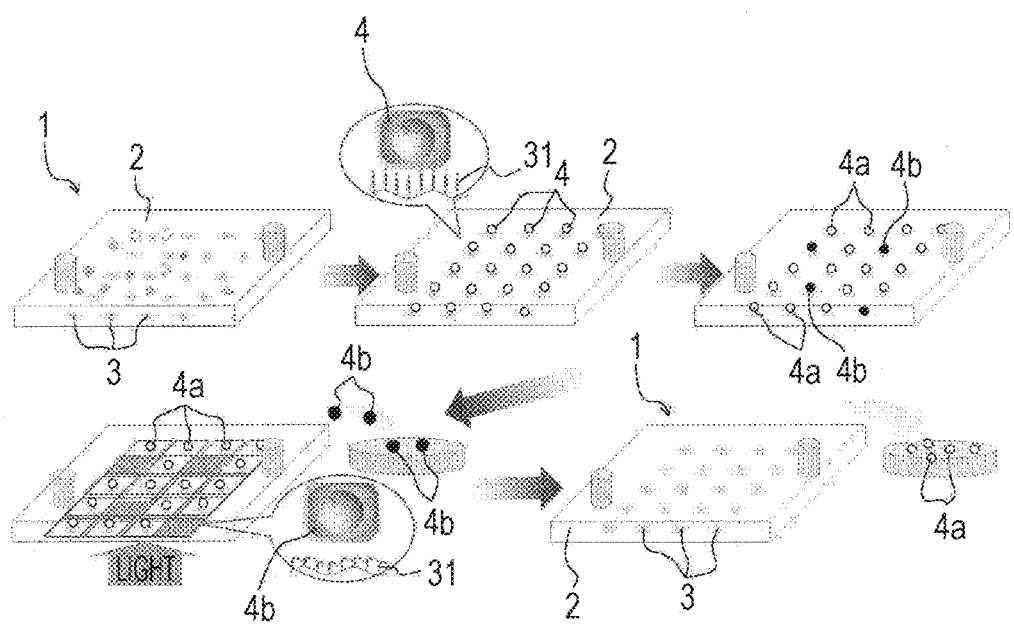
FIG. 5 is a schematic conceptual diagram schematically illustrating the method for selecting a to-be-fixed material illustrated in FIG. 4.

By this chemical introduction step S12, for example, a non-recovery target cell 4b (cell indicated by a black circle in FIG. 5) is killed, and a recovery target cell 4a (cell indicated by a white circle in FIG. 5) is not killed and can be recovered through the recovery step S16.

(3) First Light Irradiation Step

After the chemical introduction step S12 is performed, the first light irradiation step S13 for irradiating the cell 4b that has been killed in the chemical introduction step S12 with light is performed.

In this first light irradiation step S13, the non-target cell 4b is irradiated with light in a wavelength band inducing photoisomerization of a light-responsive group of the light-responsive site included in the material-fixing agent 31, corresponding to the type of the light-responsive group.

For example, in a case where the light-responsive group includes a structure of azobenzene, since the azobenzene strongly absorbs light in an ultraviolet region, the wavelength of light for irradiation is preferably within a range of 10 to 400 nm, and more preferably within a range of 340 to 380 nm.

In this first light irradiation step S13, the exposure intensity of light for irradiation only needs to be within a range that induces photoisomerization in the light-responsive site 34 and does not damage the cell 4. For example, in a case where light has a wavelength of 365 nm, the exposure intensity is preferably within a range of 1 to 1000 mW/cm$^2$.

In addition, irradiation time of light only needs to be within a range that induces photoisomerization in the light-responsive site 34 and does not damage the cell 4, and is 10 seconds to 30 minutes, for example.

Furthermore, an irradiation direction of light in the first light irradiation step S13 can be appropriately set by a person skilled in the art such that photoisomerization of the light-responsive group is induced. For example, in a case where a material of the substrate transmits light, light can be emitted from the opposite side to a surface on which the material-fixing agent is fixed. This prevents the light from being blocked by the cell 4, and photoisomerization can be performed more efficiently.

In this first light irradiation step S13, the light-responsive site 34 of the material-fixing agent 31 attached to the non-target cell 4 is photoisomerized. Therefore, a bond between the non-target cell 4 and the attachment site 35 is broken. As a result, the non-target cell 4 is detached from the substrate 2.

Here, in a case where the light-responsive group is azobenzene, by irradiation with light in an ultraviolet region, the azobenzene is isomerized from a trans-form to an unstable cis-form. As a result, a bond between the non-target cell 4 and the attachment site 35 is broken.

In this first light irradiation step S13, a method for irradiating the non-target cell 4b with light is not particularly limited, and a known method can be used.

Examples of the method include a method for selectively controlling a light irradiation position by disposing a liquid crystal shutter between a light source for performing irradiation with light and the substrate 2 and applying voltage to the liquid crystal shutter to control light transmittance, for example.

(4) Second Light Irradiation Step S14

In the selection method according to the present technology, after the first light irradiation step S13 is performed, the second light irradiation step S14 is performed.

In this second light irradiation step S14, the substrate 2 to which only the target cell 4a is attached is irradiated with light in a wavelength band inducing photoisomerization of a light-responsive group of the light-responsive site included in the material-fixing agent 31, corresponding to the type of the light-responsive group.

As in the first light irradiation step S13, for example, in a case where the light-responsive group includes a structure of azobenzene, since the azobenzene strongly absorbs light in an ultraviolet region, the wavelength of light for irradiation is preferably within a range of 10 to 400 nm, and more preferably within a range of 340 to 380 nm.

In addition, as in the first light irradiation step S13, the exposure intensity of light for irradiation in the second light irradiation step S14 only needs to be within a range that induces photoisomerization in the light-responsive site 34 and does not damage the target cell 4a. For example, in a case where light has a wavelength of 365 nm, the exposure intensity is preferably within a range of 1 to 1000 mW/cm$^2$. In addition, irradiation time of light only needs to be within a range that induces photoisomerization in the light-responsive site 34 and does not damage the target cell 4a, and is preferably 10 seconds to 30 minutes, for example.

In the second light irradiation step S14, the light-responsive site 34 of the material-fixing agent 31 attached to the target cell 4a is photoisomerized. Therefore, a bond between the target cell 4a and the attachment site 35 is broken. As a result, the target cell 4a is detached from the substrate 2.

(5) Liquid-Feeding Step

In the selection method according to the present technology, after the second light irradiation step S14 is performed, the liquid-feeding step S15 is performed.

Specifically, a buffer solution is poured into the substrate 2, and the target cell 4a detached from the substrate 2 in the second light irradiation step S14 is caused to flow out into the buffer solution to obtain an outflow fraction.

In this liquid-feeding step S15, a method for feeding a fluid such as a buffer solution is not particularly limited, and a known method can be adopted. Examples of the method include a method for feeding the fluid into the substrate 2 using a known liquid-feeding pump such as a peristaltic dosing pump, for example.

(6) Recovery Step

In the selection method according to the present technology, after the liquid-feeding step S15 is performed, the recovery step S16 is performed.

In this recovery step S16, the outflow fraction that has flowed out in the liquid-feeding step S15 is recovered as a recovery fraction. This recovery method is not particularly limited, and a known method can be adopted.

(7) Third Light Irradiation Step

In the selection method according to the present technology, in a case where the light-responsive site 34 includes a structure of azobenzene, the method preferably includes the third light irradiation step S17.

That is, as described above, when azobenzene is irradiated with ultraviolet light, the azobenzene changes the structure thereof from a trans-form to a cis-form. Meanwhile, when the azobenzene is irradiated with visible light, the azobenzene causes such a reversible change to return from the cis-form to the trans-form.

Therefore, in the first light irradiation step S13 and the second light irradiation step S14, in a case where azobenzene changes the structure thereof to a cis-form, by irradiating the azobenzene with visible light in the third light irradiation step S17, the azobenzene is caused to change the structure thereof to a trans-form reversibly.

The wavelength of light to be emitted in this third light irradiation step S17 is preferably 400 nm or more, and more preferably within a range of 400 to 500 nm. In addition, the exposure intensity of light for irradiation in the third light irradiation step S17 is preferably in a range of 1 to 200 mW/cm$^2$, for example, in a case where the light has a wavelength of 440 nm. Furthermore, irradiation time of light is preferably, for example, 5 to 1800 seconds.

Figure 4:
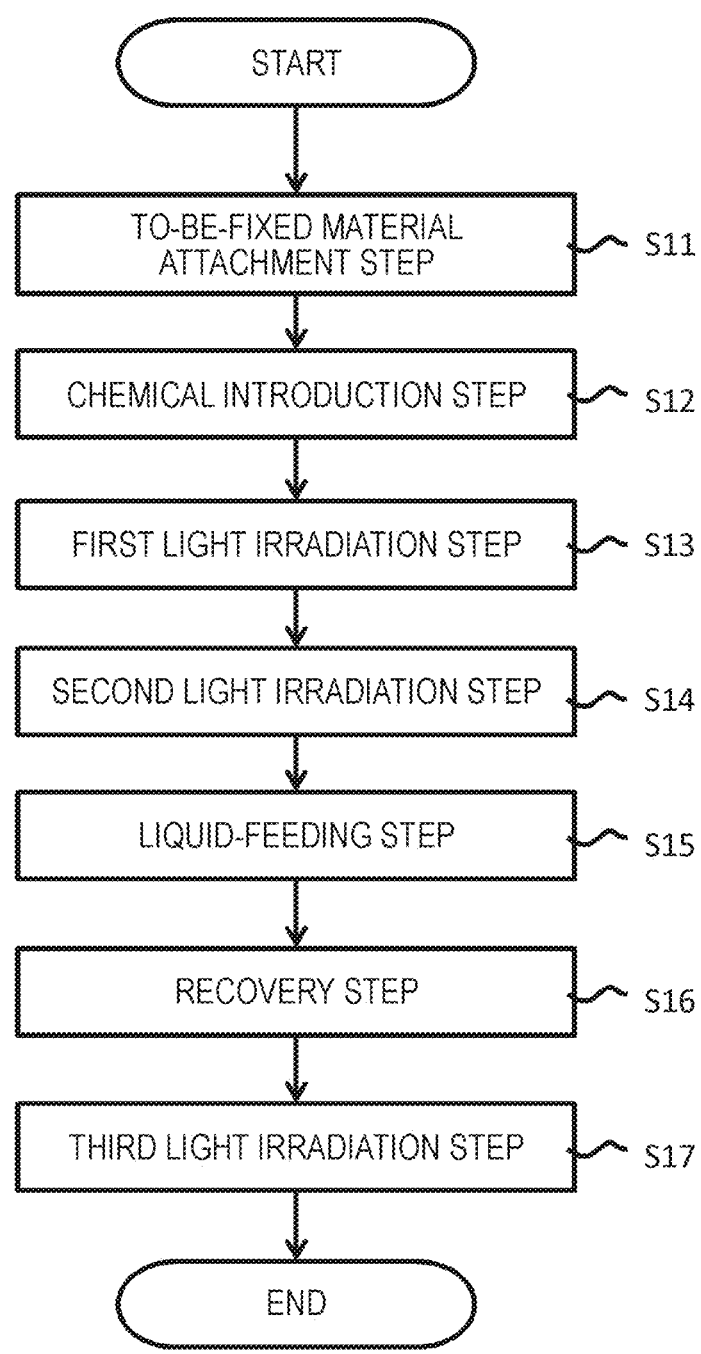
FIG. 4 is a flowchart illustrating a method for selecting a to-be-fixed material using the material-fixing substrate according to the present technology.

Incidentally, in the flowchart illustrated in FIG. 4, the third light irradiation step S17 is illustrated so as to be performed after the recovery step S16. However, if the target cell 4 is in a state of being detached in the second light irradiation step S14, for example, the third light irradiation step S17 may be performed before the liquid-feeding step S15.

In addition, it is also known that azobenzene is isomerized thermally. Therefore, instead of the third light irradiation step, a step of heating the material-fixing substrate 1 according to the present technology to realize a structural change of azobenzene may be included. However, in azobenzene, a reaction rate of photoisomerization is larger than a reaction rate of thermal isomerization. Therefore, in order to speed up the method for selecting a to-be-fixed material, a step of irradiating azobenzene with light is more preferable.

According to the above method for selecting a to-be-fixed material according to the present technology, since the substrate-bonding site 32 in the material-fixing substrate 1 includes at least a cyclic alkyne, the substrate 2 can be bonded to the material-fixing agent layer 3 without using copper as a catalyst. Therefore, for example, in a case where the to-be-fixed material 4 is a cell, damage to the cell can be reduced, and proliferation ability of the cell can be thereby maintained. In addition, copper is not required as a catalyst. Therefore, proliferation ability of a recovered cell can also be maintained.

Furthermore, in a case where the light-responsive group included in the light-responsive site 34 is azobenzene, detachment and recovery of the to-be-fixed material 4 can be repeatedly performed, and use cost can be thereby reduced.

Incidentally, in the method for selecting a to-be-fixed material according to the present technology, illustrated in FIG. 4, in the chemical introduction step S12, the non-target to-be-fixed material 4 is excluded, and the target to-be-fixed material 4 is selected.

However, the method for selecting the target to-be-fixed material 4 is not limited to the method by chemical introduction. For example, a method for pouring a fluid such as a buffer solution into the substrate 2 separately from the liquid-feeding step S15, causing a to-be-fixed material that has not been attached to the substrate 2 in the to-be-fixed material attachment step S11 to flow out of the substrate 2, then observing the to-be-fixed material 4 on the substrate 2, and subjecting the specific to-be-fixed material 4 to the first light irradiation step S13 is also considered.

Note that the material-fixing substrate according to the present technology can have the following configurations.

(1)

A material-fixing substrate having a to-be-fixed material fixed thereon via a material-fixing agent, in which the material-fixing agent includes: a substrate-bonding site that forms a covalent bond with a surface of the substrate and includes at least a cyclic alkyne; a hydrophilic site that is bonded to the substrate-bonding site; a light-responsive site that is bonded to the hydrophilic site and changes the skeleton thereof by irradiation with light; and an attachment site to which the to-be-fixed material is attached.

(2)

The material-fixing substrate according to (1), in which the cyclic alkyne has a structure selected from the group consisting of a benzocyclooctynyl group, a difluorocyclooctynyl group, a dibenzocyclooctynyl group, an azadibenzocyclooctynyl group, a biarylazacyclooctynonyl group, and derivatives thereof.

(3)

The material-fixing substrate according to (1) or (2), in which the light-responsive site has one or more structures selected from the group consisting of azobenzene, stilbene, spiropyran, spirooxazine, fulgide, cinnamate, cinnamoyl, oryzanol, and diarylethene.

(4)

The material-fixing substrate according to any one of (1) to (3), in which the hydrophilic site includes polyethylene oxide or polyalkylene oxide.

(5)

The material-fixing substrate according to any one of (1) to (4), in which the material-fixing agent has any one structural formula selected from the following chemical formulas 27 to 33.

[Chemical Formula 27]

-continued
[Chemical Formula 28]
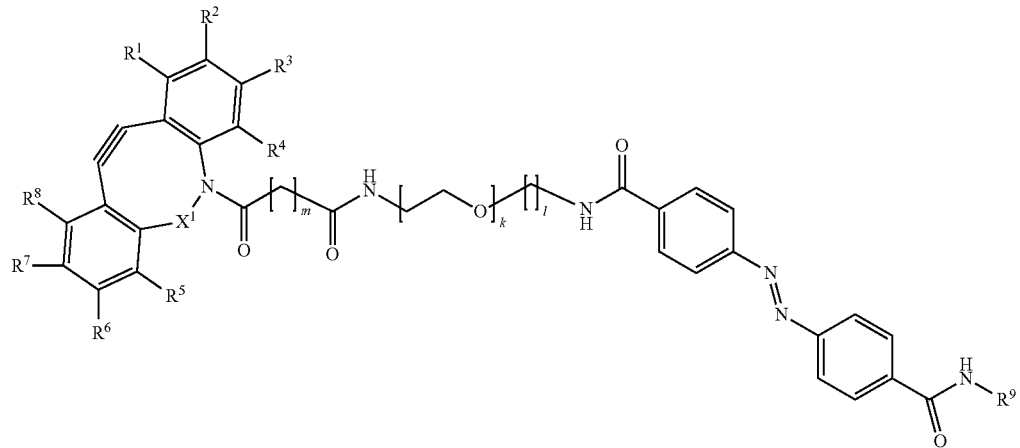
[Chemical Formula 29]
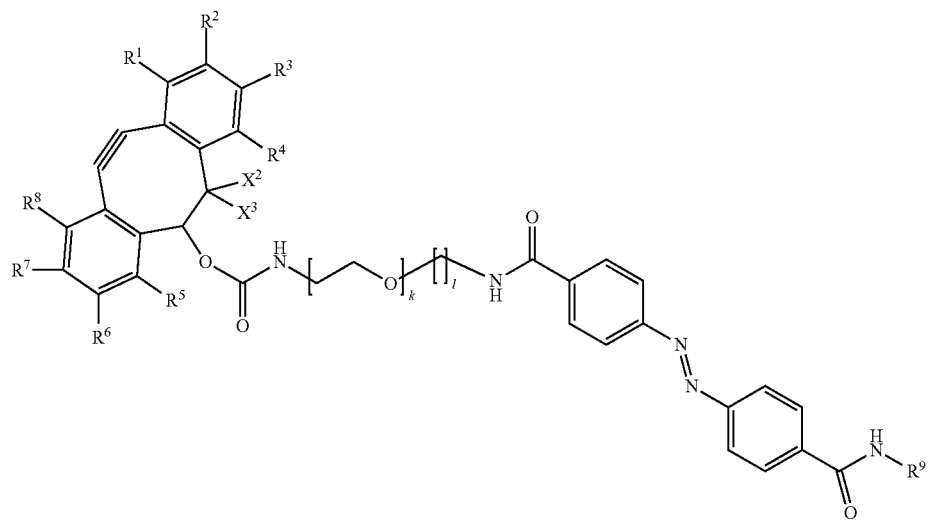
[Chemical Formula 30]
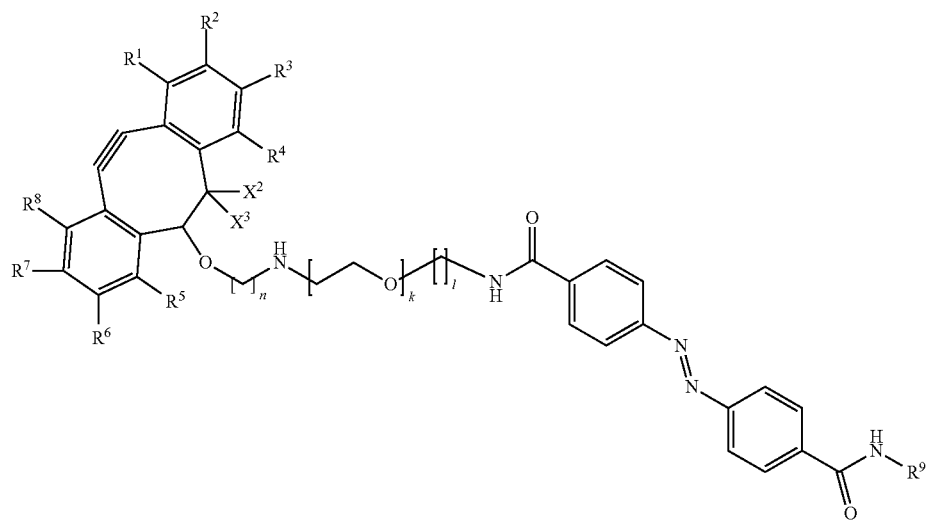

[Chemical Formula 31]

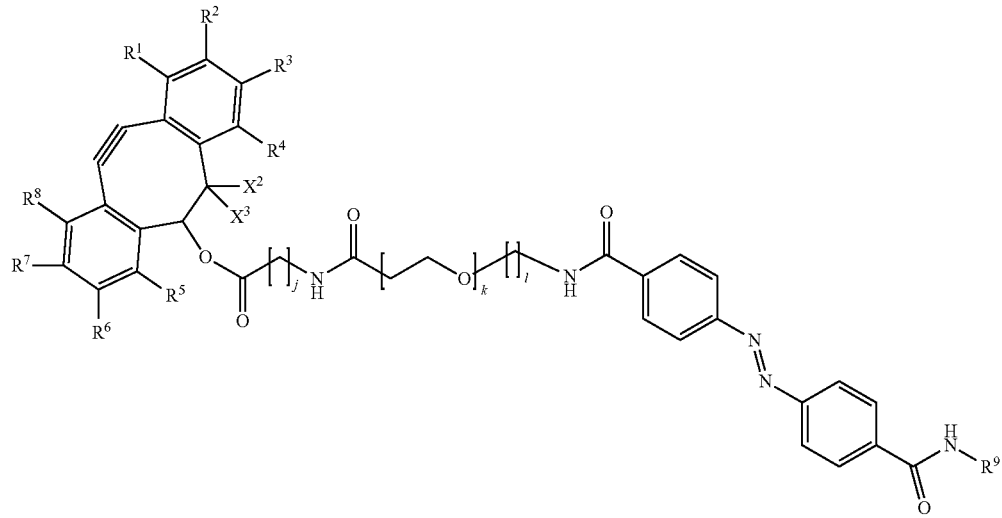

[Chemical Formula 32]

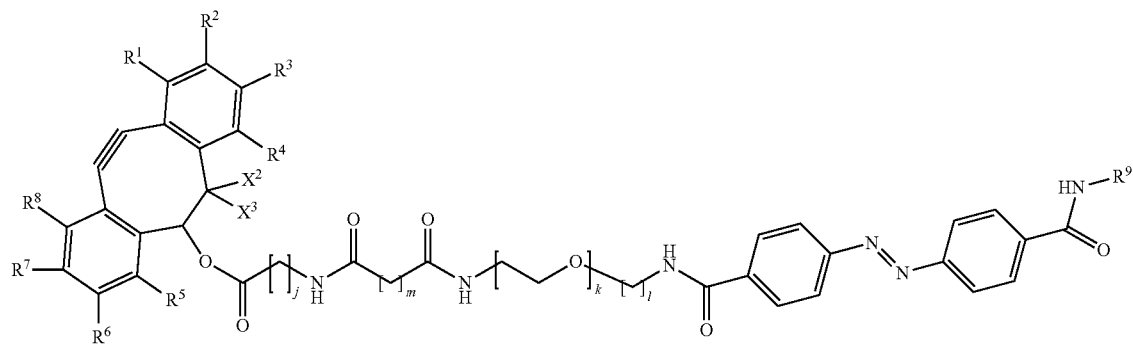

[Chemical Formula 33]

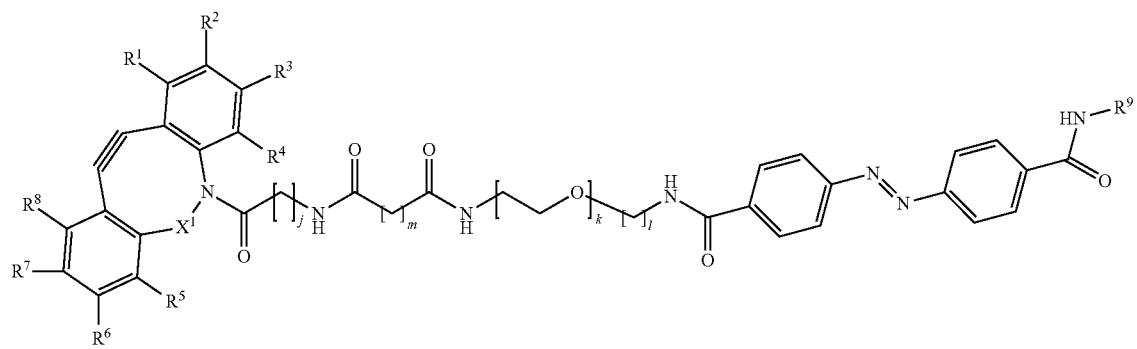

In the formulas, $R^1$ to $R^8$ are each independently selected from the group consisting of a hydrogen atom, a halogen atom, a hydroxy group, an alkoxy group, and an alkyl group having 1 to 10 carbon atoms, $R^9$ is the to-be-fixed material, $X^1$ is selected from the group consisting of $CH_2$, $C=O$, $C=N-OR^{10}$, $C=N-NR^{10}R^{11}$, $CHOR^{10}$, and $CHNHR^{10}$, $X^2$ and $X^3$ are each a hydrogen atom or a halogen atom, $R^{10}$ and $R^{11}$ are each a hydrogen atom or an alkyl group having 1 to 10 carbon atoms, j is an integer of 1 to 5, k is an integer of 2 to 100, l is an integer of 1 or 2, m is an integer of 1 to 3, and n is an integer of 2 to 100.

(6)

The material-fixing substrate according to any one of (1) to (5), in which the to-be-fixed material is at least one selected from the group consisting of an antibody, collagen, laminin, fibronectin, a protein or a peptide containing a part of the protein, and a saccharide.

(7)

The material-fixing substrate according to any one of (1) to (6), in which an azide group to be bonded to the substrate-bonding site is modified to a surface of the substrate.

REFERENCE SIGNS LIST

1 Material-fixing substrate
2 Substrate
4 To-be-fixed material
31 Material-fixing agent
32 Substrate-bonding site 33 Hydrophilic site
34 Light-responsive site
35 Attachment site

The invention claimed is:

1. A material-fixing substrate, comprising:
a specific substrate; and
a material-fixing agent, wherein the material-fixing agent includes:
   a substrate-bonding site that includes a cyclic alkyne, wherein the cyclic alkyne has a covalent bond with a surface of the specific substrate;
   a hydrophilic site bonded to the substrate-bonding site;
   a light-responsive site bonded to the hydrophilic site, wherein
      the light-responsive site is configured to change a skeleton of the light-responsive site by irradiation of light on the light-responsive site, and
      the light-responsive site includes a structure of azobenzene and at least one structure selected from the group consisting of stilbene, cinnamate, cinnamoyl, and oryzanol; and
   an attachment site to which a to-be-fixed material is attached.

2. The material-fixing substrate according to claim 1, wherein the cyclic alkyne has a structure selected from the group consisting of a benzocyclooctynyl group, a difluorocyclooctynyl group, a dibenzocyclooctynyl group, an azadibenzocyclooctynyl group, a biarylazacyclooctynonyl group, and derivatives thereof.

3. The material-fixing substrate according to claim 2, wherein the light-responsive site further includes a structure selected from the group consisting of spiropyran, spirooxazine, fulgide, and diarylethene.

4. The material-fixing substrate according to claim 3, wherein the hydrophilic site includes one of polyethylene oxide or polyalkylene oxide.

5. The material-fixing substrate according to claim 1, wherein the to-be-fixed material is at least one selected from the group consisting of an antibody, collagen, laminin, fibronectin, a protein or a peptide containing a part of the protein, and a saccharide.

6. The material-fixing substrate according to claim 5, wherein the substrate-bonding site is bonded to an azide group that is modified to the surface of the specific substrate.

7. A material-fixing agent, comprising:
a substrate-bonding site that includes a cyclic alkyne, wherein
   the cyclic alkyne has a covalent bond with a surface of a substrate, and
   the cyclic alkyne has a structure selected from the group consisting of a benzocyclooctynyl group, a difluorocyclooctynyl group, a dibenzocyclooctynyl group, an azadibenzocyclooctynyl group, a biarylazacyclooctynonyl group, and derivatives thereof;
a hydrophilic site bonded to the substrate-bonding site;
a light-responsive site bonded to the hydrophilic site, wherein
   the light-responsive site is configured to change a skeleton of the light-responsive site by irradiation of light on the light-responsive site, and
   the light-responsive site includes a structure of azobenzene and at least one structure selected from the group consisting of stilbene, cinnamate, cinnamoyl, and oryzanol; and
an attachment site to which a to-be-fixed material is attached.

* * * * *